US012376831B2

(12) United States Patent
Liu et al.

(10) Patent No.: US 12,376,831 B2
(45) Date of Patent: Aug. 5, 2025

(54) ULTRASOUND SYSTEM WITH HIGH FREQUENCY DETAIL

(71) Applicant: FUJIFILM Sonosite, Inc., Bothell, WA (US)

(72) Inventors: Kai Wen Liu, Richmond Hill (CA); Nicholas Christopher Chaggares, Whitby (CA)

(73) Assignee: FUJIFILM Sonosite, Inc., Bothell, WA (US)

( * ) Notice: Subject to any disclaimer, the term of this patent is extended or adjusted under 35 U.S.C. 154(b) by 867 days.

(21) Appl. No.: 16/183,835

(22) Filed: Nov. 8, 2018

(65) Prior Publication Data

US 2019/0133550 A1 May 9, 2019

Related U.S. Application Data

(60) Provisional application No. 62/583,416, filed on Nov. 8, 2017.

(51) Int. Cl.
*A61B 8/00* (2006.01)
*A61B 8/14* (2006.01)
(Continued)

(52) U.S. Cl.
CPC .............. *A61B 8/5246* (2013.01); *A61B 8/14* (2013.01); *A61B 8/145* (2013.01); *A61B 8/463* (2013.01);
(Continued)

(58) Field of Classification Search
CPC ............. G01S 15/8952; G01S 15/8979; G01S 7/52074; G01S 7/52085; G01S 7/5202;
(Continued)

(56) References Cited

U.S. PATENT DOCUMENTS 4,915,115 A * 4/1990 Sasaki ................. G01S 15/8979
600/441
5,165,413 A * 11/1992 Maslak ............... G01S 7/52074
600/441
(Continued)

FOREIGN PATENT DOCUMENTS

CN 102665569 A 9/2012
CN 106903037 A 6/2017
(Continued)

OTHER PUBLICATIONS

KR20140107648A translation (Year: 2014).*
(Continued)

*Primary Examiner* — Christopher Koharski
*Assistant Examiner* — Renee C Langhals
(74) *Attorney, Agent, or Firm* — Colby Nipper PLLC

(57) ABSTRACT

An ultrasound imaging system is configured to interface with a dual frequency ultrasound transducer having one or more low frequency ultrasound arrays and one or more high frequency ultrasound arrays. The imaging system produces driving pulses for both the high frequency ultrasound array and the low frequency ultrasound imaging array. Analog echo signals are processed to produce a low frequency ultrasound image and a high frequency ultrasound image that are simultaneously displayed. Tissue shown in the high frequency ultrasound image is a portion of the tissue shown in the low frequency ultrasound image.

36 Claims, 6 Drawing Sheets

(51) Int. Cl.
  *G01S 7/52* (2006.01)
  *G01S 15/89* (2006.01)
(52) U.S. Cl.
  CPC ............... *A61B 8/523* (2013.01); *A61B 8/54* (2013.01); *G01S 7/52074* (2013.01); *G01S 7/52085* (2013.01); *G01S 15/8952* (2013.01); *A61B 8/4483* (2013.01); *A61B 8/4494* (2013.01); *A61B 8/465* (2013.01); *A61B 8/469* (2013.01); *G01S 15/8979* (2013.01)
(58) Field of Classification Search
  CPC ......... A61B 8/14; A61B 8/145; A61B 8/4483; A61B 8/4494; A61B 8/463; A61B 8/465; A61B 8/469; A61B 8/523; A61B 8/5246; A61B 8/54; A61B 8/5207
  See application file for complete search history.

(56) References Cited

U.S. PATENT DOCUMENTS

| | | | |
|---|---|---|---|
| 5,882,306 | A | 3/1999 | Ramamurthy et al. |
| 5,904,652 | A | 5/1999 | Gilbert et al. |
| 6,500,122 | B1 * | 12/2002 | Washburn ........... G01S 7/52073 600/443 |
| 11,169,265 | B2 * | 11/2021 | Pang .................... B06B 1/0622 |
| 11,506,770 | B2 | 11/2022 | Ouzounov |
| 2002/0157472 | A1 * | 10/2002 | Stephens ............. B06B 1/0633 73/626 |
| 2004/0102702 | A1 | 5/2004 | Shimazaki |
| 2005/0203416 | A1 | 9/2005 | Angelsen et al. |
| 2006/0270935 | A1 * | 11/2006 | Ariff .................... G06Q 30/04 600/437 |
| 2007/0073154 | A1 * | 3/2007 | Karasawa ............ A61B 8/4488 600/459 |
| 2007/0078347 | A1 | 4/2007 | Srinivasan et al. |
| 2007/0083119 | A1 * | 4/2007 | Adachi ................. A61B 8/00 600/437 |
| 2007/0213614 | A1 | 9/2007 | Suzuki et al. |
| 2007/0232924 | A1 | 10/2007 | Karasawa |
| 2007/0239014 | A1 * | 10/2007 | Yoshikawa ............ A61B 8/13 600/455 |
| 2009/0118619 | A1 | 5/2009 | Oshiki |
| 2009/0182237 | A1 * | 7/2009 | Angelsen ............... B06B 1/064 600/459 |
| 2010/0036244 | A1 | 2/2010 | Angelsen et al. |
| 2010/0087737 | A1 * | 4/2010 | Iwama ................. G01S 7/5202 600/447 |
| 2010/0204579 | A1 | 8/2010 | Yoshida et al. |
| 2010/0228129 | A1 | 9/2010 | Osumi |
| 2011/0087104 | A1 * | 4/2011 | Moore ................ G01S 7/52071 600/447 |
| 2013/0144166 | A1 * | 6/2013 | Specht ................. A61B 8/4444 600/441 |
| 2014/0039317 | A1 | 2/2014 | Sato |
| 2014/0371587 | A1 * | 12/2014 | Vanderby ............. A61B 8/5246 600/443 |
| 2015/0141828 | A1 * | 5/2015 | Yoshiara ............... A61B 8/483 600/447 |
| 2015/0164473 | A1 | 6/2015 | Kim et al. |
| 2017/0164923 | A1 * | 6/2017 | Matsumoto ........... A61B 5/026 |
| 2017/0209126 | A1 * | 7/2017 | Yoshimura ............ A61B 1/04 |
| 2017/0282215 | A1 | 10/2017 | Chaggares et al. |
| 2018/0246208 | A1 * | 8/2018 | Dittmer .............. G01S 7/52084 |
| 2018/0306919 | A1 | 10/2018 | Van Rens et al. |
| 2019/0133550 | A1 | 5/2019 | Liu et al. |
| 2020/0256971 | A1 | 8/2020 | Huang et al. |

FOREIGN PATENT DOCUMENTS

| | | | |
|---|---|---|---|
| EP | 0 520 397 | A2 | 12/1992 |
| EP | 2 287 632 | A1 | 2/2011 |
| JP | H07163559 | | 6/1995 |
| JP | 08-294487 | A | 11/1996 |
| JP | H08294488 | | 11/1996 |
| JP | 2004195091 | | 7/2004 |
| JP | 2004-313290 | A | 11/2004 |
| JP | 2007-068918 | A | 3/2007 |
| JP | 2010-536502 | A | 12/2010 |
| JP | 2013-507227 | A | 3/2013 |
| JP | 2014-506811 | A | 3/2014 |
| JP | 2014-207990 | A | 11/2014 |
| JP | 2015-084976 | A | 5/2015 |
| JP | 2017067713 | A * | 4/2017 |
| JP | 2017164408 | A | 9/2017 |
| KR | 20140107648 | A * | 9/2014 |
| WO | WO 2015/151972 | A1 | 10/2015 |
| WO | WO 2017/042304 | A1 | 3/2017 |
| WO | WO 2017/089376 | A1 | 6/2017 |
| WO | WO 2017/173414 | A1 | 10/2017 |

OTHER PUBLICATIONS

JP 2017067713 A—translation (Year: 2017).*
Avdal et al., "Effects of Reverberations and Clutter Filtering in Pulsed Doppler using Sparse Sequences," IEEE Transactions on Ultrasonics, Ferroelectrics And Frequency Control, IEEE, 62(5):828-838 (2015).
Partial European Search Report dated Oct. 2, 2020 in Application No. EP 20177366.
Supplementary Partial European Search Report dated Oct. 1, 2020 in Application No. EP 18875529.
Supplementary European Search Report dated Feb. 15, 2021 in Application No. EP 18875529.
U.S. Appl. No. 16/183,886, filed Nov. 8, 2018.
International Search Report and Written Opinion mailed Mar. 6, 2019 in International Application No. PCT/US2018/059809.
"Final Office Action", U.S. Appl. No. 16/183,886, filed Aug. 12, 2022, 15 pages.
"Non-Final Office Action", U.S. Appl. No. 16/183,886, filed May 24, 2023, 27 pages.
"Foreign Office Action", CN Application No. 201880072087.X, Sep. 23, 2023, 27 pages.
"Foreign Office Action", CA Application No. 3,081,019, Oct. 13, 2023, 5 pages.
"Foreign Office Action", JP Application No. 2023-047030, Nov. 14, 2023, 8 pages.
"Foreign Office Action", EP Application No. 18875529.2, Nov. 22, 2023, 6 pages.
"Final Office Action", U.S. Appl. No. 16/183,886, filed Aug. 16, 2023, 19 pages.
"Foreign Office Action", CN Application No. 201880072087.X, Jun. 17, 2023, 22 pages.
"Foreign Office Action", KR Application No. 10-2020-7016257, Jun. 23, 2023, 17 pages.
"Foreign Office Action", EP Application No. 20177366.0, Nov. 28, 2023, 7 pages.
"Foreign Office Action", JP Application No. 2023-047030, Apr. 9, 2024, 5 pages.
"Foreign Office Action", CA Application No. 3,081,019, Apr. 1, 2025, 5 pages.

* cited by examiner

ULTRASOUND SYSTEM WITH HIGH FREQUENCY DETAIL

PRIORITY

This application claims the benefit, under 35 U.S.C. § 119(e), of U.S. Provisional Patent Application No. 62/583,416, filed 8 Nov. 2017, which is incorporated herein by reference.

TECHNICAL FIELD

The disclosed technology relates to imaging systems and to ultrasound imaging systems in particular.

BACKGROUND

High frequency and ultrahigh frequency ultrasound (10-50 MHz center frequency) is often used for pre-clinical and clinical imaging applications. One advantage of high frequency ultrasound is its detailed resolution. For 50 MHz center frequency transducers, objects as small as 30 µm can be imaged. However, there are drawbacks to imaging with such high frequencies.

The higher the frequency of the ultrasound signal, the more attenuation there is and this limits the imaging depth. For example, in soft tissue, signals from a 2 MHz transducer can image penetrate over 20 cms but signals from a 50 MHz transducer have a usable depth range of less than 1 cm.

In order to achieve better lateral resolution, the array element spacing has to be as small as possible. A transducer element pitch of less than 1λ is preferred for linear arrays and less than ½ λ is preferred for phased arrays. Using a 256 element 50 MHz array as an example, an element spacing of 1λ, requires that the footprint of the array be less than 1 cm. The size of the array on its field of view is analogous to a microscope where the higher the magnification, the smaller the field of view will be.

With current ultrasound imaging systems, an operator has to switch between two different types of transducers to view tissue with low and high frequency ultrasound. The use of a low frequency (LF) transducer takes advantage of the deeper and wider field of view that can be used to image a larger area of tissue with less detail. Conversely, the use of a high frequency (HF) transducer allows the operator to image a smaller area of tissue in greater detail. Having to switch between transducers is not very convenient and takes practice to find a landmark tissue structure in the same orientation in order to match two different imaging studies. Also, because imaging studies obtained by swapping transducers are acquired in different time slices, there is little valuable time related information that can be obtained.

DETAILED DESCRIPTION OF THE PREFERRED EMBODIMENTS

To address the problems described above, the disclosed technology relates to an ultrasound imaging system that is designed to support simultaneous high and low frequency ultrasound imaging transducers. Two synchronous or asynchronous images obtained with the same transducer can be constructed and displayed on the screen to allow a user to view tissue in a region of interest and a subset of the tissue with additional detail.

Figure 1:
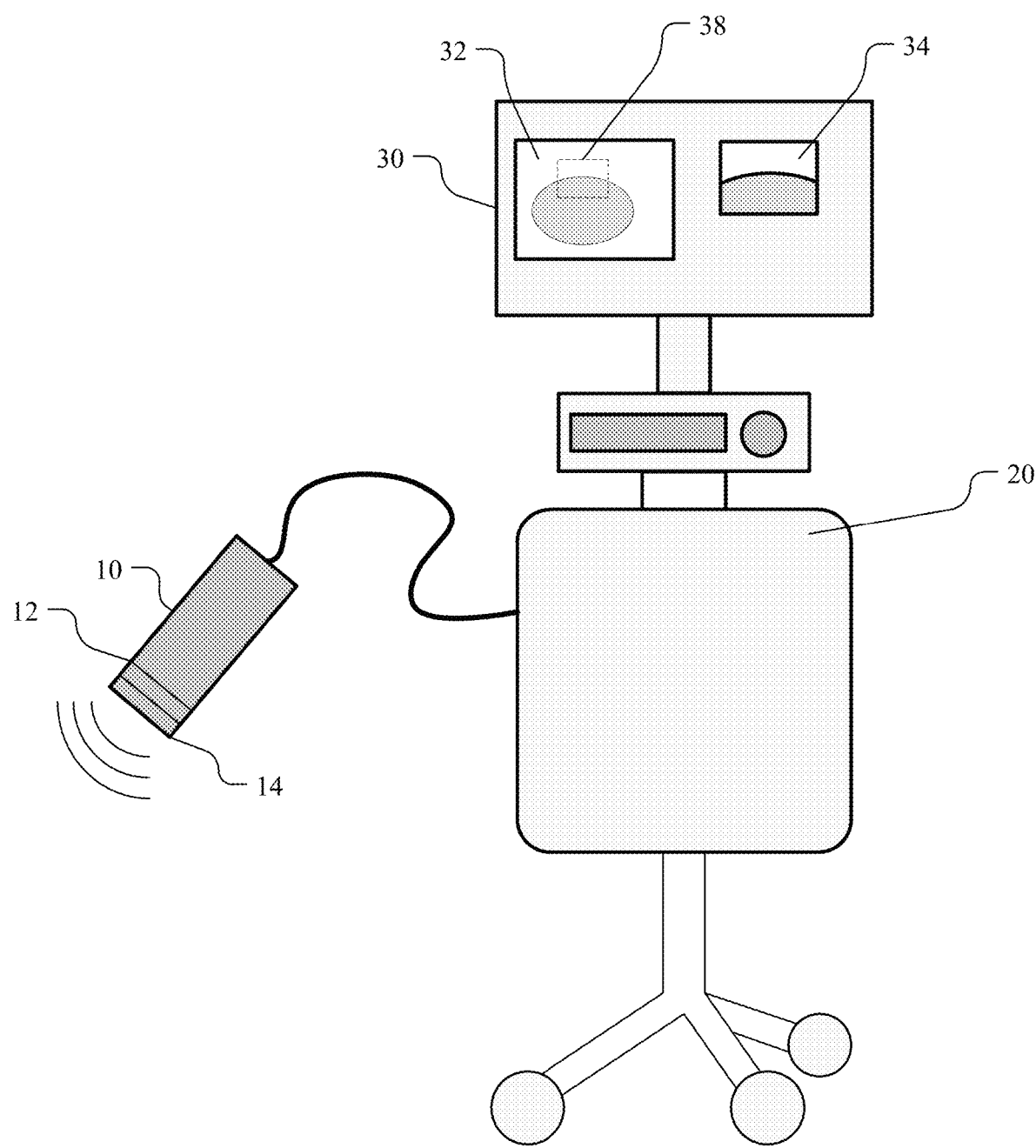
FIG. 1 is a simplified block diagram of a dual frequency ultrasound imaging system in accordance with an embodiment of the disclosed technology.

As shown in FIG. 1, an ultrasound imaging system includes a dual frequency transducer 10. The dual frequency transducer has one or more low frequency ultrasound transducer arrays 12 and one or more high frequency transducer arrays 14. Numerous configurations of the dual frequency transducer are possible. For example, the high frequency transducer can be positioned in-line (behind or ahead) with the low frequency transducer. One suitable dual frequency transducer design is described in commonly-assigned U.S. patent application Ser. No. 16/051,060, filed 31 Jul. 2018, which is incorporated herein by reference. Alternatively, the one or more low frequency transducers can be positioned offset to (flanking) the high frequency transducer. One suitable dual frequency transducer design is described in commonly assigned PCT Application No. WO/2017/173414A1 and United States Patent Publication No. 20170282215, which are herein incorporated by reference in their entireties. These applications describe a transducer design where a low frequency transducer array is positioned behind a high frequency transducer array but is angled in one or more of the azimuthal and elevation directions so that the low frequency transducer array is facing in a slightly different direction to reduce reflections. In another embodiment, one or more low frequency transducer arrays can be positioned to flank a high frequency transducer array so that beams from the low frequency transducer arrays intersect the imaging plane of the high frequency transducer array. Such a design is described in U.S. Provisional Patent application No. 62/553,497 filed Sep. 1, 2017 and is also incorporated by reference in its entirety.

An ultrasound imaging system 20 provides signals or pulses that drive the dual frequency transducer 10 and processes the detected echo signals. The ultrasound imaging system 20 includes electronics that are adapted to interface with both the high and low frequency transducers and process the detected echo signal in order to produce images of tissue being examined. In one embodiment, the imaging system 20 produces images on a video display 30 that include an image 32 from the electronic echo signals that are produced by the low frequency transducer 12 and an image 34 from the electronic echo signals that are produced by the high frequency transducer 14. The image 32 from the low frequency transducer has less detail but covers a greater field of view. Conversely, the image 34 from the high frequency transducer has much more detail but covers a smaller field of view. The images 32, 34 can be shown side by side or the image 34 can take up part of the image 32 or vice versa in a manner similar to a picture in picture window in a television system. Either image can be removed from the display so that the user can view just one of the images at a time if desired. In some embodiments, the area of tissue encompassed in the image 34 from the high frequency transducer is shown on the image 32 with a dashed box 38 or other graphic symbol that allows the user to understand which section of tissue in the low frequency image 32 is being shown in the high frequency ultrasound image 34.

In some embodiments, the operator of the ultrasound imaging system can interact with one or more user controls (keyboard, trackball, sliders, touch screen, touch pad, touch wheel etc.) on the imaging system 20 to move the position of the dashed box 38 within the low frequency image 32 in order to change tissue area that is shown in the high frequency image 34 (if the area of the dashed box is smaller than the field of view of the high frequency transducer). In some embodiments, the ultrasound imaging system 20 is designed with very wide bandwidth transmit (TX) and receive (RX) channels so that same channels can be used to process signals from either of the HF and LF transducer arrays. It can also be designed with separate HF TX/RX channels and LF TX/RX channels that are connected via multiplexers.

Figure 2:
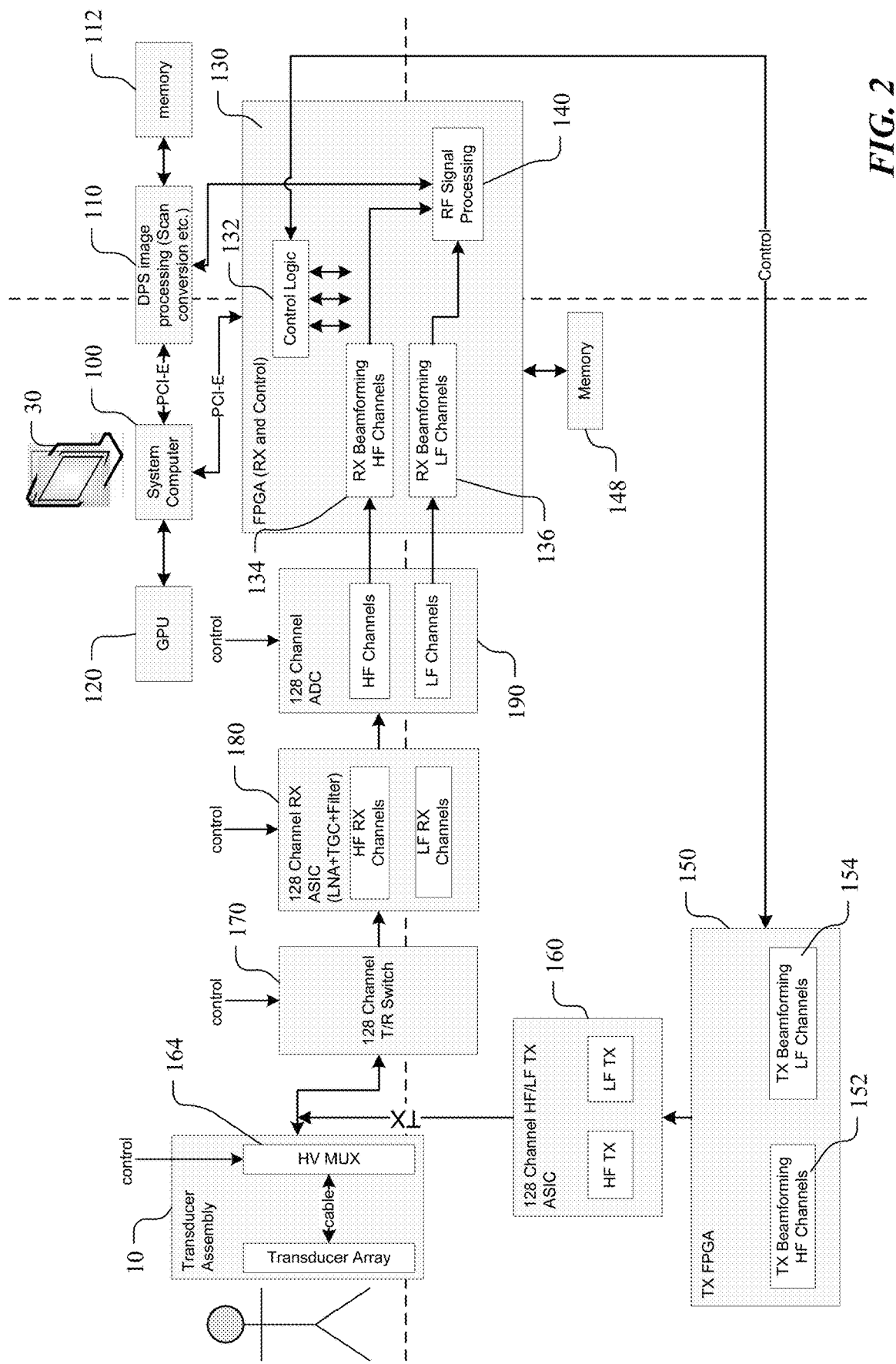
FIG. 2 is a more detailed block diagram of a dual frequency ultrasound imaging system in accordance with an embodiment of the disclosed technology.

FIG. 2 shows additional detail of a dual frequency ultrasound imaging system in accordance with an embodiment of the disclosed technology. The imaging system includes a system computer 100 (e.g. one or more CPUs) that is configured to execute programmed instructions to cause the dual frequency transducer 10 to transmit and receive ultrasound signals. The computer system 100 interfaces with one or more digital signal processors 110 that are configured to convert ultrasound data into pixel data that can be displayed on the video monitor 30 and/or stored in a local or remote computer readable memory device 112 (hard drive, flash drive etc.) A graphics processor 120 is also in communication with the computer system 100 to perform computational tasks related to the display of ultrasound data on the video monitor 30.

The computer system 100 is in communication with a field programmable gate array (FPGA) 130 that controls the transmission and reception of ultrasound signals from the transducer 10. The FPGA 130 includes control logic 132 that controls the timing of transmit pulses that are provided to the transducers. The FGPA 130 also includes logic 134 for high frequency beamforming and logic 136 for low frequency beamforming. Outputs of the beamforming logic 134, 136 are supplied to RF signal processing logic 140 that is configured to process the radio frequency (RF) ultrasound signals to down convert the beamformed ultrasound signals to a lower baseband frequency. The output of the RF signal processing logic 140 supplies signals to the DSP 110 that operates in conjunction with the graphics processor unit 120 to perform such tasks as gain adjustment, filtering, envelope detection, dynamic range compression (log compression in most cases) and additional 2D processing followed by scan conversion in order to generate the low and high frequency ultrasound images. The details of the FPGA logic and techniques for processing ultrasound imaging signals in order to produce corresponding ultrasound images on a video monitor are considered to be known to those of ordinary skill in the art.

A transmit FPGA 150 includes logic 152 that is configured to generate the drive pulses for the low frequency transducer 12 and logic 154 that is configured to generate the drive pulses for the high frequency transducer 14. In one embodiment, the transmit FPGA 150 generates 128 drive pulses that can be delivered to 128 transducer elements in the low frequency transducer or to the 128 elements in the high frequency transducer or to a split between transducer elements of the low and high frequency transducers as indicated by control signals received from the control logic 132. Of course, it will be appreciated that transducer arrays with a larger or smaller number of transducer elements could also be used. In addition, it is not necessary that the low and high frequency transducers have the same number of transducer elements.

In one embodiment, the HF and LF drive pulses are transmitted at the same trigger point and delivered to different transducer elements. The pulses applied to the low and high frequency transducer elements need not be identical but can be tailored in accordance with the frequency range of the transducer. In some embodiments, the HF and LF TX drive pulses are transmitted at the same time or with delays but in the same pulse-echo sequence.

The HF and LF TX pulses will be on top of each other during transmit and receive. If the HF and LF frequency ranges are far away enough between each other, LF and HF images can be acquired at the same time. For example, with a 2 MHz/20 MHz dual frequency array, each having 100% bandwidth, the received acoustic echoes will have both 1-3 MHz low frequency components and 10-30 MHz high frequency components. The arrays will naturally function as band pass filters, but further filtering can also be performed in analog or digitally.

Drive pulses from the transmit FPGA 150 are applied to a 128 channel high frequency/low frequency transmit ASIC 160 that operates to increase the voltage of the drive signals and otherwise condition the pulses in a manner that will cause selected transducer elements to produce ultrasonic acoustic waves into the tissue of the subject.

In one exemplary embodiment, the ASIC 160 is a quad, five-level RTZ, high-voltage, ultra high-speed pulser part number HDL6V5541HF available from Hitachi/SII. The ASIC 160 consists of logic interfaces, level translators, MOSFET gate drive buffers, and high-voltage, high-current MOSFETs. The ASIC pulse waveforms are controlled by 1.8V to 5V CMOS logic interface. The frequency range of the pulse waveforms is from 1 MHz to 100 MHz.

The conditioned drive pulses from the transmit ASIC 160 are applied to an N:1 multiplexer 164 that in one embodiment is located in the housing of the dual frequency transducer 10. The N:1 multiplexer 164 connects, for example, each of 128 input lines to a designated transducer element. If the low frequency transducer has 128 elements and the high frequency transducer has 128 elements, then a 2:1 multiplexer could be used to connect each of the 128 input lines to either a low or a high frequency transducer element. If a 256 element low frequency transducer and a 128 element high frequency transducer are used, then a 3:1 multiplexer could be used to direct the drive pulses to either transducer elements in the lower or upper half of the low frequency transducer or to the elements of the high frequency transducer. Other combinations including larger or smaller low and high frequency transducer arrays are possible.

In the embodiment shown, control of the multiplexer 164 is provided by signals from the control logic 132 in the FPGA 130. The control logic 132 in the FPGA 130 is configured to direct how many low frequency and high frequency transmit pulses are produced by the TX FPGA 150, when the pulses are produced and to set the positions of the multiplexer 164 so that the correct drive pulses are delivered to the correct transducer elements.

In the receive path, the ultrasound imaging system includes a transmit/receive switch 170 that is controlled by the control logic 132 in the FPGA 130 to protect receive circuitry in the imaging system from the high voltage pulses that are applied to the transducer elements during the transmit phase. In one embodiment, the transmit/receive switch 170 has 128 input channels that can be connected to selected transducer elements in the low frequency transducer or to transducer elements in the high frequency transducer or can be placed in an open state whereby the switch is disconnected from any transducer elements during the transmit phase. The echo signals that are received on each channel of the transmit/receive switch 170 are controlled by the position of the multiplexer 164. In some embodiments, the low frequency ultrasound transducer is not very responsive to the high frequency ultrasound signals. Similarly, the high frequency ultrasound transducer is not very sensitive to low frequency ultrasound signals. Therefore, the transducers themselves perform the first level of filtering the signals.

Further processing of the signals received on the channels the T/R switch 170 is performed by a receive ASIC 180 that performs such tasks as low noise amplification, time gain control that varies the level of amplification with time gain compensation to compensate for the attenuation of ultrasound signals in tissue. In addition, the receive ASIC performs filtering to remove artifacts.

In one embodiment, the receive ASIC 180 is a high performance, wide-bandwidth ultrasound front-end receiver and filter. The ASIC 180 includes a low noise amplifier (LNA) that is optimized for high dynamic range and low distortion to enable Tissue Harmonic Imaging (THI). A High Pass Filter (HPF) has a 4th order response with precision frequency tuning to improve performance in THI. There is also a $2^{nd}$ order mode of operation for the HPF used to reduce power during other modes of operation. Transmit gain control provides additional gain range control and has an additional precision clipper to prevent Low Pass Filter (LPF) overload and distortion. The Low Pass Filter (LPF) has both 2 and 4 pole modes of operation and also has precision tuning to enable fine channel to channel phase matching for high resolution imaging. An output buffer stage has a programmable gain control for additional optimization control of the overall signal path gain. The configuration of the ASIC 180 is through SPI (Serial Peripheral Interface) bus Control signals from the control logic 132 inform the receive ASIC 180 whether the signals received on any particular channel should be processed as a low or high frequency ultrasound signal. The processing steps performed for each channel are generally similar. However, filter coefficients, coefficients for time gain compensation amplification and other signal processing steps may be set for each particular channel depending on whether the channel receives a low or high frequency ultrasound signal.

In some embodiments, the signals from the HF channels are group together and go through the same processes but with different parameters to generate the HF images. They can use separate processing resources (such as dedicated FPGA logic resources) or share the same resources but be time interleaved. The drawback of firing both the low and high frequency transducer elements at the same time is that even though the arrays can function as a band pass filter during receive, the low frequency component of the received signals could still be significant enough to overwhelm the receive signal path for the HF signals.

Signals from the receive ASIC 180 are supplied to an analog to digital (A/D) converter 190. The A/D converter 190 receives signals from the control logic 132 that inform the A/D converter 190 whether the analog signal received is a high or low frequency ultrasound signal. Depending on the frequency of the echo signal received, the appropriate settings to the A/D converter 190 are selected and the analog echo signals are converted into a corresponding stream of digital samples.

The ADC converter is a low-power, high-performance, 16-channel, analog-to-digital converter (ADC) such as an ADS52J90 A/D converter available from Texas Instruments. The conversion rate of the A/D converter goes up to a maximum of 100 MSPS in 10-bit mode. The device can be configured to accept 8, 16, or 32 inputs. In 8 input mode, two ADCs convert the same input in an interleaved manner, resulting in an effective sampling rate that is twice the ADC conversion rate which is up to 200 MHz. The ADC outputs are serialized and output through a LVDS interface along with a frame clock and a high-speed bit clock. The configuration interface is an SPI bus. In one embodiment, a multiplexer (not shown) precedes the A/D converter 190 so that selected channels of the 128 channels from the receive ASIC 180 are applied to the inputs of the A/D converter 190.

Digital samples of the low and high frequency echo signals on the input channels to the FPGA 130 are supplied to beamformer logic 134, 136 that combine the signals with techniques such as delay and sum to produce a sample representing the echo intensity or other tissue characteristic such as signal power or phase shift at a point on a beamline that will be used to construct an image. Although the beamformer logic blocks 134, 136 are shown as separate logic blocks for ease of understanding, it will be appreciated that in implementation, a single beamformer logic circuit with control inputs to indicate whether an input channel should be processed as a high or low frequency ultrasound signal may be configured in the FPGA 130. Beamformed signals corresponding to the low and high frequency ultrasound echoes are delivered to the RF signal processing logic 140 where they are downconverted to a baseband frequency and then supplied to the DSP image processor 110 to assemble into a low frequency ultrasound image and a high frequency ultrasound image.

As indicated above, the ultrasound signals from a low frequency transducer can penetrate deeper into tissue to be examined and the transducer has a larger field of view. However, the details that can be imaged with such a low frequency transducer (e.g. 1-10 MHz) are limited. Small features in the tissue or quickly moving tissue/fluids cannot be resolved using the signals from the low frequency transducer. On the other hand, the high frequency transducer can image the tissue with greater resolution/speed but has a smaller field of view. In order to give a user the ability to view additional detail in an area that is imaged with a low frequency transducer, the disclosed technology operates to produce and simultaneously display images created by the low and high frequency transducers. The images produced from the high frequency transducer typically include more detail than the images produced from the low frequency transducer. Because the transducers are located in the same transducer housing, the area of tissue imaged with the high frequency transducer is a subset of the area imaged by the low frequency transducer. In addition, the temporal differences between when the low and high frequency images of the tissue are obtained can be minimized thereby allowing the same tissue area to be seen in each image contemporaneously.

Figure 3A:
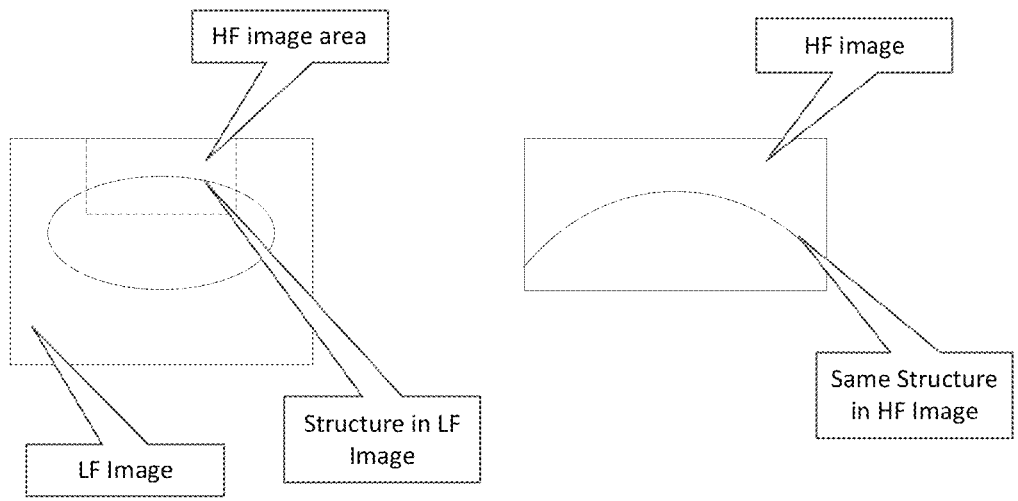
FIG. 3A shows a combined low and high frequency display in accordance with one embodiment of the disclosed technology.

FIG. 3A shows one embodiment of a combined low and high frequency image that are shown on a display. On the left side of the display is a low frequency ultrasound image obtained with echo signals received from the low frequency transducer. On the right side of the display is a more detailed, high frequency ultrasound image that is obtained with ultrasound signals received by the high frequency transducer. In the embodiment shown, the low frequency ultrasound image includes a visual marker or graphic such as a dashed box that is overlaid on a portion of the low frequency ultrasound image that shows the area of the tissue that is included in the high frequency ultrasound image.

If the field of view of the high frequency transducer is larger than the area encompassed by the visual marker, then the user can interact with a user control to change the position of the visual marker on the low frequency image and change the area of tissue included in the high frequency ultrasound image. The position of the marker can be changed with an input device such as a keyboard, trackball, joystick, touch sensitive screen, touchpad, touch wheel or the like on the ultrasound imaging machine. As will be appreciated by those skilled in the art, changing the position of the graphic on the low frequency ultrasound image correlates to changes to one or both of the transmit and receive beamforming signal parameters in order to change the region of tissue that is shown in the high frequency ultrasound image.

Figure 3B:
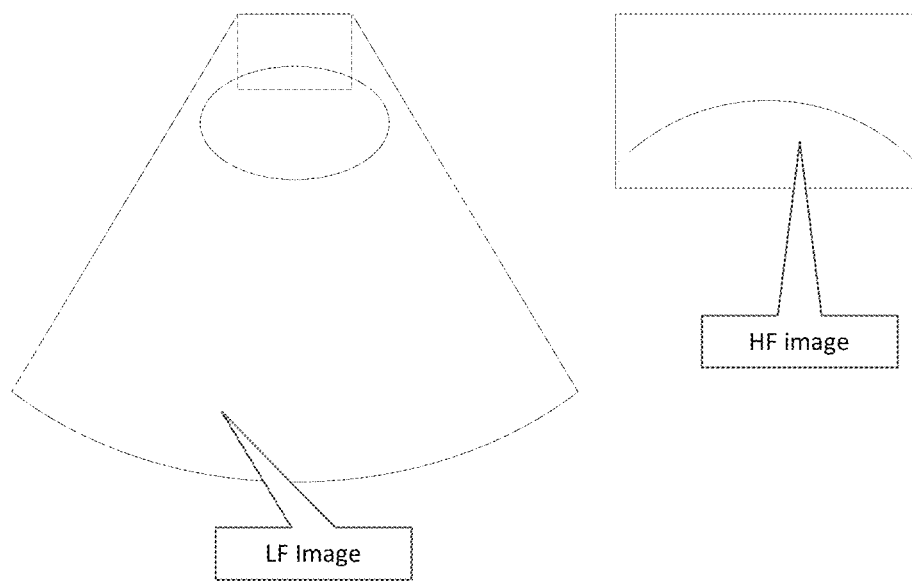
FIG. 3B shows another embodiment of a combined low and high frequency display in accordance with the disclosed technology.

FIG. 3B shows a low frequency ultrasound image obtained with a convex shaped low frequency ultrasound transducer or a phased array low frequency transducer. The low frequency ultrasound image has a conventional fan-like shape over a field of view that is wider at it maximum width than a width of the ultrasound transducer. Within the low frequency ultrasound image is the visual marker or graphic showing the area of tissue that is displayed in a high frequency ultrasound image obtained from signals transmitted from and received by the high frequency transducer. Again, the position of the visual marker or graphic can be moved in the low frequency ultrasound image to change the area of tissue that is displayed in the high frequency ultrasound image.

Figure 4A:
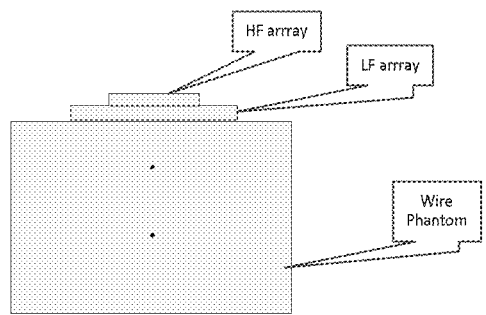
FIG. 4A shows a simplified diagram of a test set up for obtaining low and high frequency ultrasound images in accordance with an embodiment of the disclosed technology.
Figure 4B:
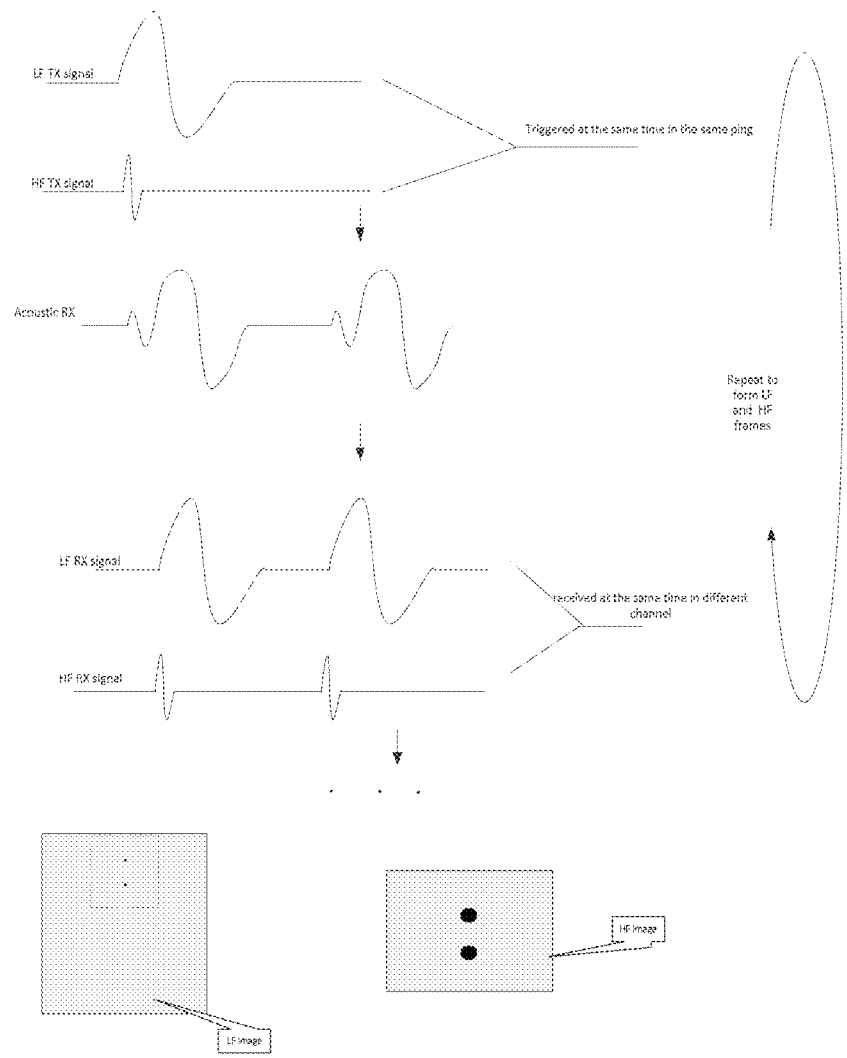
FIG. 4B is a timing diagram of a method of obtaining low and high frequency images of tissue in accordance with an embodiment of the disclosed technology.
Figure 4C:
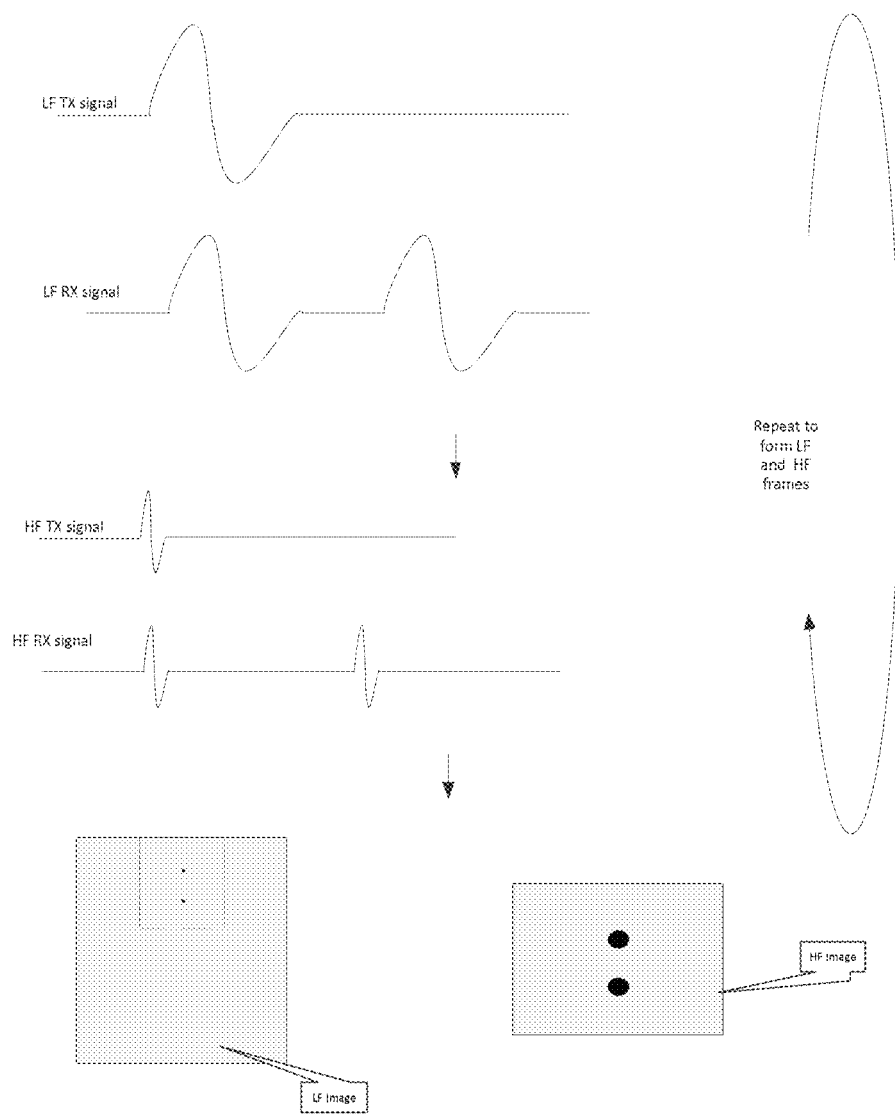
FIG. 4C is a timing diagram of a method of obtaining low and high frequency images of tissue in accordance with an embodiment of the disclosed technology.
Figure 4D:
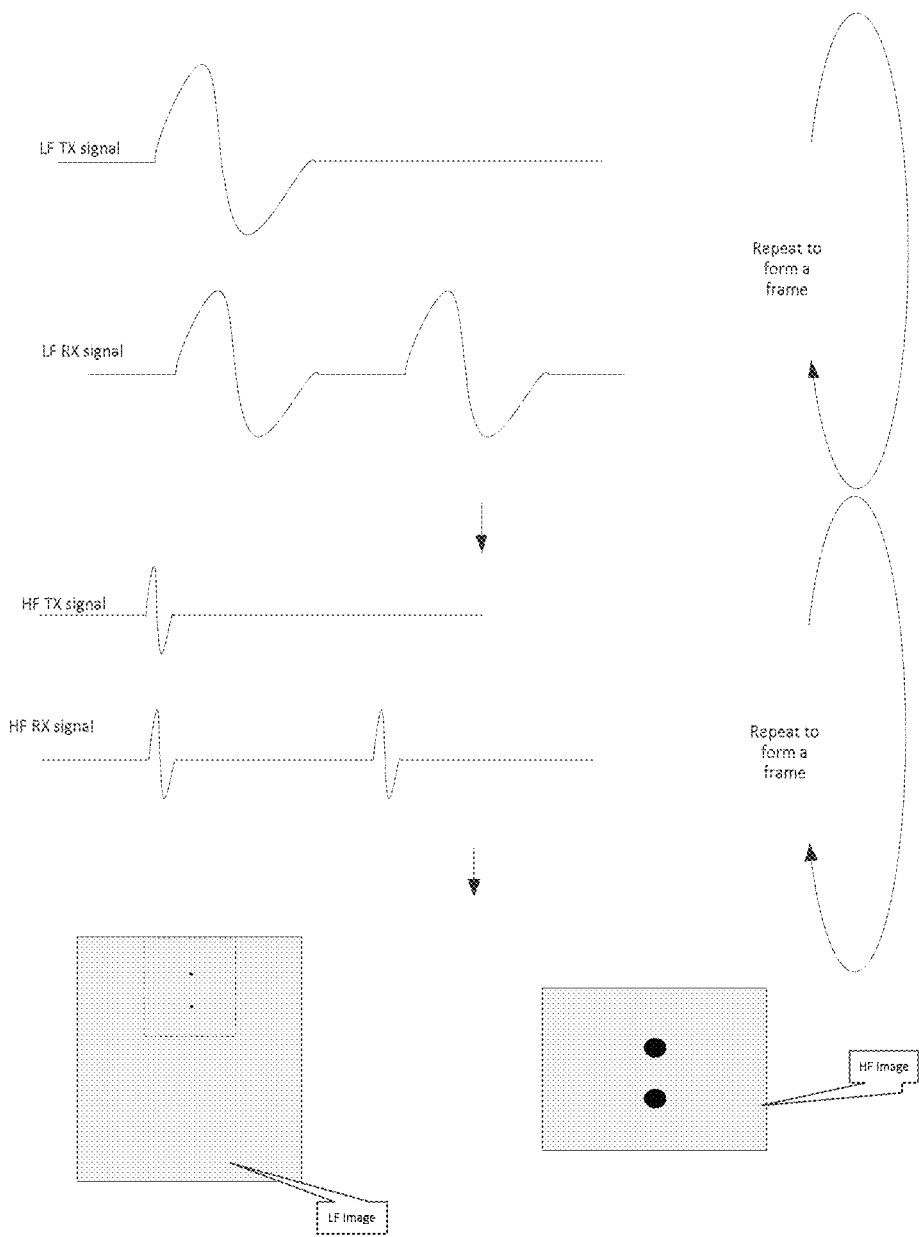
FIG. 4D is a timing diagram of a method of obtaining low and high frequency images of tissue in accordance with an embodiment of the disclosed technology.

FIGS. 4B-4D illustrate several alternative methods of triggering high frequency and low frequency transmit pulses in accordance with the disclosed technology. In one embodiment, high frequency and low frequency transmit pulses can be generated by the same trigger so that the individual transducer driving pulses are aligned or are generated with defined time offsets. The corresponding echo signals are received by the high frequency transducer array and the low frequency transducer array at, or nearly at, the same time. Because both arrays are bandwidth limited, received echo signals in a frequency range that are not in the array's receive bandwidth are mostly filtered out by the array itself. Further filtering can also be applied to generate echo signal data used to produce the low frequency and high frequency images. In some embodiments, the number of echo signals that can be processed is less than the number of elements in the low frequency or high frequency transducers. Therefore, multiple sets of transmit pulses may be required to produce an image of the tissue. The position of the multiplexor 164 as controlled by the control logic 132 directs the transmit pulses to the correct transducer elements depending on whether low frequency, high frequency or combined low/high frequency ultrasound signals are being obtained by the imaging system.

In some embodiments, the number of transducer elements used to obtain images during simultaneous LF/HF imaging can be pre-defined based on the size of the different transducers, the desired imaging depth, the ultrasound imaging mode (e.g. B-mode, Doppler mode, power mode etc.) Alternatively, the number of transducer elements used in the low and high frequency transducers can be adjusted by the user. For example, the user can increase the number of high frequency transducer elements used if more detail is desired in the high frequency image with a corresponding decrease in the number of transducer elements to be used to produce the low frequency image. Alternatively, the number of elements used to create the low frequency image can be increased and with a corresponding decrease in the number of elements used in creating the high frequency ultrasound image.

One suitable test setup is shown in FIG. 4A where a dual frequency transducer is positioned over a water bath with phantom wires in the beam path of the transducers. A low frequency image of the bath area is obtained with the low frequency ultrasound transducer array while a more detailed image of the wire phantoms is obtained with the high frequency transducer array.

As shown in FIG. 4B, the low frequency and high frequency transmit pulses are transmitted at the same time and the corresponding echo signals are received at the same time. Depending on the processing speed of the imaging system, it is possible to transmit multiple high frequency ultrasound pulses between successive low frequency ultrasound pulses. This allows fast moving tissue to be captured with the high frequency ultrasound while a larger area of tissue that doesn't move as fast can be captured with the low frequency ultrasound.

In another embodiment as shown in FIG. 4C, transmit pulses for the high frequency transducer array are interleaved between transmit pulses for the low frequency transducer array. In this embodiment, the system scans each beam line twice, once using low frequency ultrasound signals and again using high frequency ultrasound signals.

Yet another method in accordance with the disclosed technology is to interleave low frequency and high frames as shown in FIG. 4D. For example, a complete low frequency ultrasound frame can be constructed followed by a high frequency ultrasound frame or vice versa. The frame data can be stored in a memory until both frames are ready to be simultaneously displayed on the video monitor. In particular embodiments, the frames may be ready for simultaneous display based on the timestamps of each frame.

This disclosed technology is not limited to traditional 2D line-to-line scanning. It can also be used in plane wave imaging where transmit pulses are not focused and RF channel data is acquired during receive. In plane wave imaging, all or groups of the transducer elements are excited at the same time and signals generated in response to the corresponding echo signals from each of the elements are digitized and stored in an RF memory (not shown). Receive beamforming is performed offline so as not to delay the frame rate in real time.

As indicated above, the low and high frequency ultrasound images are not limited to 2D B mode images. Either or both images can be any image mode, for example: a low frequency 2D image with a color flow high frequency image; a low frequency color flow image with a high frequency color flow image etc.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus.

A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium also can be, or can be included in, one or more separate physical components or media (e.g., multiple CDs, disks, or other storage devices). The operations described in this specification can be implemented as operations performed by a data processing apparatus on data stored on one or more computer-readable storage devices or received from other sources.

The terms "programmed processor, processing circuitry or programmed logic" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit).

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code).

The processes and logic flows described in this specification can be performed by one or more programmed processors or processor logic executing one or more computer programs or configured to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks or non-volatile memory logic. However, a computer need not have such devices. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

What is claimed is:

1. An ultrasound imaging system, comprising:
a dual frequency transducer comprising a low frequency transducer and a high frequency transducer, the high frequency transducer having a field of view that is smaller than and located within a field of view of the low frequency transducer;
processing circuitry for receiving echo signals produced by the low frequency transducer and the high frequency transducer and for producing a low frequency ultrasound image with echo signals received by the low frequency transducer and a high frequency ultrasound image with echo signals received by the high frequency transducer, the low frequency ultrasound image representing an area of tissue corresponding to the field of view of the low frequency transducer, the high frequency ultrasound image representing a subset of the area of tissue, the low frequency ultrasound image including a graphic that indicates a location corresponding to the subset of the area of tissue represented in the high frequency ultrasound image;
a display on which the low frequency ultrasound image and the high frequency ultrasound image are simultaneously displayed in a side-by-side manner with the low frequency ultrasound image positioned on a first side of the display and the high frequency ultrasound image positioned on a second side, opposite of the first side, of the display; and
a control with which a user can adjust a position of the graphic in the low frequency ultrasound image to change the area that is represented in the high frequency ultrasound image, the field of view of the high frequency transducer being greater than an area encompassed by the graphic, the position of the graphic being adjustable within the field of view of the high frequency transducer, the control usable by the user to increase a number of first transducer elements used in the high frequency transducer with a corresponding decrease in a number of second transducer elements to be used to produce the low frequency ultrasound image or increase the number of the second transducer elements used in the low frequency transducer with a corresponding decrease in the number of the first transducer elements to be used to produce the high frequency ultrasound image.

2. The ultrasound imaging system of claim 1, wherein the processing circuitry is configured to drive the low frequency transducer and the high frequency transducer at the same time.

3. The ultrasound imaging system of claim 1, wherein the processing circuitry is configured to drive the low frequency transducer and the high frequency transducer with interleaved driving pulses.

4. The ultrasound imaging system of claim 3, wherein the processing circuitry is configured to generate multiple driving pulses for the high frequency transducer between successive driving pulses for the low frequency transducer.

5. The ultrasound imaging system of claim 1, wherein the processing circuitry is configured to drive the low frequency transducer and the high frequency transducer such that a frame of ultrasound data obtained with the low frequency transducer is interleaved with a frame of ultrasound data obtained with the high frequency transducer.

6. The ultrasound imaging system of claim 5, further comprising a memory configured to store the frame of ultrasound data obtained with the low frequency transducer and the frame of ultrasound data obtained with the high frequency transducer until both frames are ready for simultaneous display on the display.

7. The ultrasound imaging system of claim 1, further comprising:
control logic for controlling a circuit that generates transmit pulses for the low frequency transducer and the high frequency transducer; and
a multiplexer that receives control signals from the control logic to selectively connect the transmit pulses to transducer elements in the low frequency transducer and the high frequency transducer.

8. The ultrasound imaging system of claim 1, further comprising a single set of transmit channels and a single set of receive channels, wherein:
the single set of transmit channels is capable of generating transmit pulses for the low frequency transducer and the high frequency transducer; and
the single set of receive channels is capable of receiving signals from either of the low frequency transducer and the high frequency transducer.

9. The ultrasound imaging system of claim 1, wherein:
the low frequency transducer acts as a band pass filter of high frequency ultrasound signals; and
the high frequency transducer acts as a band pass filter of low frequency ultrasound signals.

10. The ultrasound imaging system of claim 1, wherein the low frequency ultrasound image is in a first image mode and the high frequency ultrasound image is in a second image mode.

11. The ultrasound imaging system of claim 10, wherein the first image mode and the second image mode each comprise:
a two-dimensional B mode image;
a plane wave image; or
a color flow image.

12. The ultrasound imaging system of claim 1, wherein the high frequency ultrasound image is of a higher resolution than the low frequency ultrasound image.

13. A method of operating an ultrasound imaging system that includes a dual frequency transducer comprising a low frequency transducer and a high frequency transducer, comprising:
transmitting ultrasound signals from the low frequency transducer and the high frequency transducer;
processing received echo signals produced by the low frequency transducer and the high frequency transducer;
producing a low frequency ultrasound image with echo signals received by the low frequency transducer and a high frequency ultrasound image with echo signals received by the high frequency transducer, the low frequency ultrasound image representing an area of tissue, the high frequency ultrasound image representing a subset of the area of tissue, the low frequency ultrasound image including a graphic that indicates a location corresponding to the subset of the area of tissue represented in the high frequency ultrasound image, the high frequency transducer having a field of view greater than an area encompassed by the graphic;
simultaneously displaying the low frequency ultrasound image and the high frequency ultrasound image in a side-by-side manner with the low frequency ultrasound image displayed on a first side of a display and the high frequency ultrasound image displayed on a second side, opposite of the first side, of the display; and
providing a control with which a user can adjust a position of the graphic in the low frequency ultrasound image to change the area that is represented in the high frequency ultrasound image, the position of the graphic being adjustable within the field of view of the high frequency transducer, the control usable by the user to increase a number of first transducer elements used in the high frequency transducer with a corresponding decrease in a number of second transducer elements to be used to produce the low frequency ultrasound image or increase the number of the second transducer elements used in the low frequency transducer with a corresponding decrease in the number of the first transducer elements to be used to produce the high frequency ultrasound image.

14. The method of claim 13, wherein the low frequency transducer and the high frequency transducer are driven at the same time.

15. The method of claim 13, wherein the low frequency transducer and the high frequency transducer are driven with interleaved driving pulses.

16. The method of claim 15, wherein multiple driving pulses for the high frequency transducer are driven between successive driving pulses for the low frequency transducer.

17. The method of claim 13, wherein the low frequency transducer and the high frequency transducer are driven such that a frame of ultrasound data obtained with the low frequency transducer is interleaved with a frame of ultrasound data obtained with the high frequency transducer.

18. The method of claim 17, wherein the frame of ultrasound data obtained with the low frequency transducer and the frame of ultrasound data obtained with the high frequency transducer are stored in a memory of the ultrasound imaging system until both frames are ready for simultaneous display on the display.

19. The method of claim 13, wherein the transmitting ultrasound signals is performed using:
control logic for controlling a circuit that generates transmit pulses for the low frequency transducer and the high frequency transducer; and
a multiplexer that receives control signals from the control logic to selectively connect the transmit pulses to the second transducer elements in the low frequency transducer and the first transducer elements in the high frequency transducer.

20. The method of claim 13, wherein the transmitting ultrasound signals is performed using a single set of transmit channels and a single set of receive channels, wherein:
the single set of transmit channels is capable of generating transmit pulses for the low frequency transducer and the high frequency transducer; and
the single set of receive channels is capable of receiving signals from either of the low frequency transducer and the high frequency transducer.

21. The method of claim 13, wherein:
the low frequency transducer acts as a band pass filter of high frequency ultrasound signals; and
the high frequency transducer acts as a band pass filter of low frequency ultrasound signals.

22. The method of claim 13, wherein the low frequency ultrasound image is in a first image mode and the high frequency ultrasound image is in a second image mode.

23. The method of claim 22, wherein the first image mode and the second image mode each comprise:
a two-dimensional B mode image;
a plane wave image; or
a color flow image.

24. The method of claim 13, wherein the high frequency ultrasound image is of a higher resolution than the low frequency ultrasound image.

25. One or more computer-readable non-transitory storage media embodying software operable when executed by one or more computing devices of an ultrasound imaging system that includes a dual frequency transducer including a low frequency transducer and a high frequency transducer to:
transmit ultrasound signals from the low frequency transducer and the high frequency transducer, the high frequency transducer having a field of view that is smaller than and located within a field of view of the low frequency transducer;
process received echo signals produced by the low frequency transducer and the high frequency transducer, the received echo signals processed to produce a low frequency ultrasound image with echo signals received by the low frequency transducer and produce a high frequency ultrasound image with echo signals received by the high frequency transducer, the low frequency ultrasound image representing an area of tissue corresponding to the field of the view of the low frequency transducer, the high frequency ultrasound image representing a subset of the area of tissue, the low frequency ultrasound image including a graphic that indicates a location corresponding to the subset of the area of tissue represented in the high frequency ultrasound image, the field of view of the high frequency transducer being greater than an area encompassed by the graphic;
simultaneously display the low and high frequency ultrasound images in a side-by-side manner with the low frequency ultrasound image positioned on a first side of a display and the high frequency ultrasound image positioned on a second side, opposite of the first side, of the display; and
provide a control with which a user can adjust a position of the graphic in the low frequency ultrasound image to change the area that is represented in the high frequency ultrasound image, the position of the graphic being adjustable within the field of view of the high frequency transducer, the control usable by the user to increase a number of first transducer elements used in the high frequency transducer with a corresponding decrease in a number of second transducer elements to be used to produce the low frequency ultrasound image or increase the number of the second transducer elements used in the low frequency transducer with a corresponding decrease in the number of the first transducer elements to be used to produce the high frequency ultrasound image.

26. The computer-readable non-transitory storage media of claim 25, wherein the low frequency transducer and the high frequency transducer are driven at the same time.

27. The computer-readable non-transitory storage media of claim 25, wherein the low frequency transducer and the high frequency transducer are driven with interleaved driving pulses.

28. The computer-readable non-transitory storage media of claim 25, wherein multiple driving pulses for the high frequency transducer are driven between successive driving pulses for the low frequency transducer.

29. The computer-readable non-transitory storage media of claim 25, wherein the low frequency transducer and the high frequency transducer are driven such that a frame of ultrasound data obtained with the low frequency transducer is interleaved with a frame of ultrasound data obtained with the high frequency transducer.

30. The computer-readable non-transitory storage media of claim 29, wherein the frame of ultrasound data obtained with the low frequency transducer and the frame of ultrasound data obtained with the high frequency transducer are stored in a memory of the ultrasound imaging system until both frames are ready for simultaneous display on the display.

31. The computer-readable non-transitory storage media of claim 25, wherein the media is further operable to transmit ultrasound signals using:
control logic for controlling a circuit that generates transmit pulses for the low frequency transducer and the high frequency transducer; and
a multiplexer that receives control signals from the control logic to selectively connect the transmit pulses to transducer elements in the low frequency transducer and the high frequency transducer.

32. The computer-readable non-transitory storage media of claim 25, wherein the media is further operable to transmit ultrasound signals using a single set of transmit channels and a single set of receive channels, wherein:
the single set of transmit channels is capable of generating transmit pulses for the low frequency transducer and the high frequency transducer; and
the single set of receive channels is capable of receiving signals from either of the low frequency transducer and the high frequency transducer.

33. The computer-readable non-transitory storage media of claim 25, wherein:
the low frequency transducer acts as a band pass filter of high frequency ultrasound signals; and
the high frequency transducer acts as a band pass filter of low frequency ultrasound signals.

34. The computer-readable non-transitory storage media of claim 25, wherein the low frequency ultrasound image is in a first image mode and the high frequency ultrasound image is in a second image mode.

35. The computer-readable non-transitory storage media of claim 34, wherein the first image mode and the second image mode each comprise:
a two-dimensional B mode image;
a plane wave image; or
a color flow image.

36. The computer-readable non-transitory storage media of claim 25, wherein the high frequency ultrasound image is of a higher resolution than the low frequency ultrasound image.

\* \* \* \* \*